United States Patent

Mackay et al.

[11] Patent Number: 4,726,194
[45] Date of Patent: Feb. 23, 1988

[54] TRANSFER SYSTEM

[75] Inventors: Murdo J. N. Mackay; James Hossack, both of Glasgow, Scotland

[73] Assignee: Fern Developments Limited, Glasgow, Scotland

[21] Appl. No.: 937,492

[22] Filed: Dec. 3, 1986

[30] Foreign Application Priority Data

Dec. 5, 1985 [GB] United Kingdom ............... 8529979

[51] Int. Cl.⁴ ............................................. F17C 7/02
[52] U.S. Cl. .................................................... 62/55
[58] Field of Search ........................................... 62/55

[56] References Cited

U.S. PATENT DOCUMENTS

| 3,126,711 | 3/1964 | Miller | 62/55 |
| 3,386,256 | 6/1968 | Alexander | 62/55 |
| 3,418,822 | 12/1968 | Massey | 62/55 |
| 3,433,028 | 3/1969 | Klee | 62/55 |
| 3,548,607 | 12/1970 | Pillsbury, Jr. et al. | 62/55 |
| 3,706,208 | 12/1972 | Kadi et al. | 62/55 |
| 3,729,946 | 5/1973 | Massey | 62/55 |
| 3,750,414 | 8/1973 | Heftman | 62/55 |
| 3,777,501 | 12/1973 | Sharp et al. | 62/55 |
| 3,878,690 | 4/1975 | Bell et al. | 62/55 |

Primary Examiner—Ronald C. Capossela
Attorney, Agent, or Firm—Ratner & Prestia

[57] ABSTRACT

A transfer system for use in transferring cryogen from a source to a point of use, comprising a flexible conduit for through flow of cryogenic fluid, heating means external of the flexible conduit arranged to provide heat to a wall of the conduit, and control means associated with said heating means for maintaining the temperature of said wall of the conduit at a level whereby cryogenic fluid flowing through the conduit in maintained in Leidenfrost flow.

3 Claims, 5 Drawing Figures

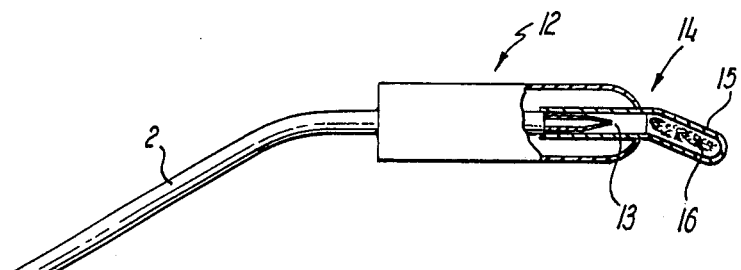
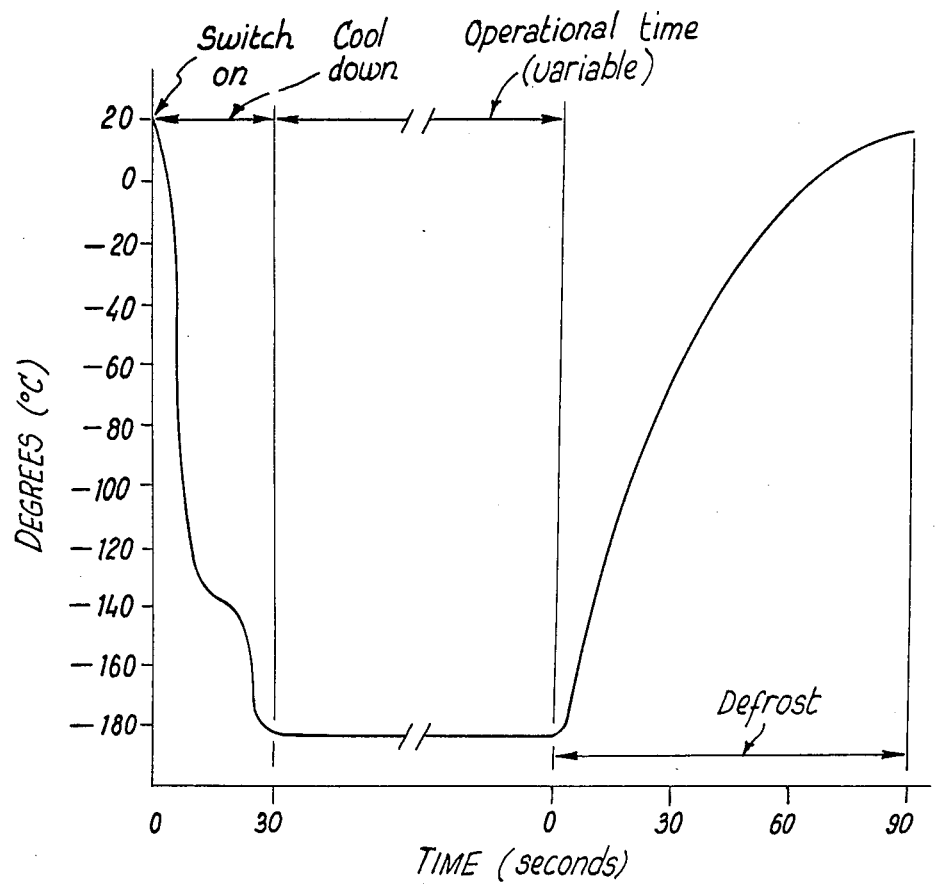

TRANSFER SYSTEM

This invention relates to a system for use in the transfer of a cryogen between a reservoir and a point of use.

BACKGROUND OF THE INVENTION

In industry, and in particular semiconductor manufacturing, cryogenic fluids are often employed when it is desired to cool a tool or a workpiece to a very low temperature. This cooling is normally achieved by the application of a cryogen such as liquid nitrogen to the object to be cooled. The cryogen may be supplied to an operator from a central reservoir, or from a well insulated supply pipe, through flexible tubing. Due to the very low temperature of the cryogen the tubing becomes hard and brittle and attracts condensation. This hardness of the tubing causes inconvenience to the operator and the condensation collecting on the tubing presents a hazard to operators of electrical machinery or tools as well as being highly inconvenient.

Cryoprobes form the operating portion in the use of cryoganic fluids, and take the form of a chamber into which the cryogenic fluid is fed, the chamber having a wall through which heat exchange can take place between the cryogenic fluid and the object to be cooled. Existing forms of cryoprobes, however, have the disadvantage that this heat exchange causes the cryogenic fluid to boil in the area adjacent the chamber wall, which creates in that area a low-temperature gas. This has an insulating effect between the chamber wall and the main body of the cryogenic fluid, with the result that heat exchange for further evaporation of the cryogenic fluid is hampered. This in turn reduces the cooling effect of the cryoprobe.

SUMMARY OF IN THE INVENTION

According to the present invention there is provided a transfer system for use in transferring cryogen from a source to a point of use, comprising a flexible conduit for through flow of cryogenic fluid, heating means external of the flexible conduit arranged to provide heat to a wall of the conduit, and control means associated with said heating means for maintaining the temperature of said wall of the conduit at a level whereby cryogenic fluid flowing through the conduit in maintained in Leidenfrost flow.

The heating means may be in the form of a heating wire helically wound around the conduit. Gas may be passed over the wire to distribute the heat along the conduit.

Alternatively the heating means may be in the form of heated gas which is passed over the surface of the conduit.

Preferably also, the conduit is contained within a second flexible conduit which forms an envelope so that gas may pass through the envelope and over the conduit. The gas which passes between the envelope and the conduit may for example be exhaust cryogen which has been vapourised, or may be externally supplied air.

Further according to the present invention there is provided a cryoprobe comprising a chamber for cryogenic fluid, means for introducing cryogenic fluid into the chamber, the chamber having a wall across which heat exchange can take place, and material within the chamber which increases significantly the internal surface area of the chamber.

Embodiments of the present invention will now be described by way of example with reference to the accompanying drawings, in which:

BRIEF DESCRIPTION OF THE DRAWINGS

FIG. 4 is a sectional side view of a cryoprobe of this invention; and

FIG. 5 is a graph showing the rate of cooling, maintenance of operating temperature and rate of defrosting attained by the cryoprobe of FIG. 4.

Referring to FIGS. 1 and 2 a first embodiment of a transfer system 1 for use in the transfer of cryogen from a liquid cryogen reservoir to a point of use comprises a flexible tube 2 through which liquid cryogen 6 flows, contained within a second, larger flexible tube 3.

Figure 1:
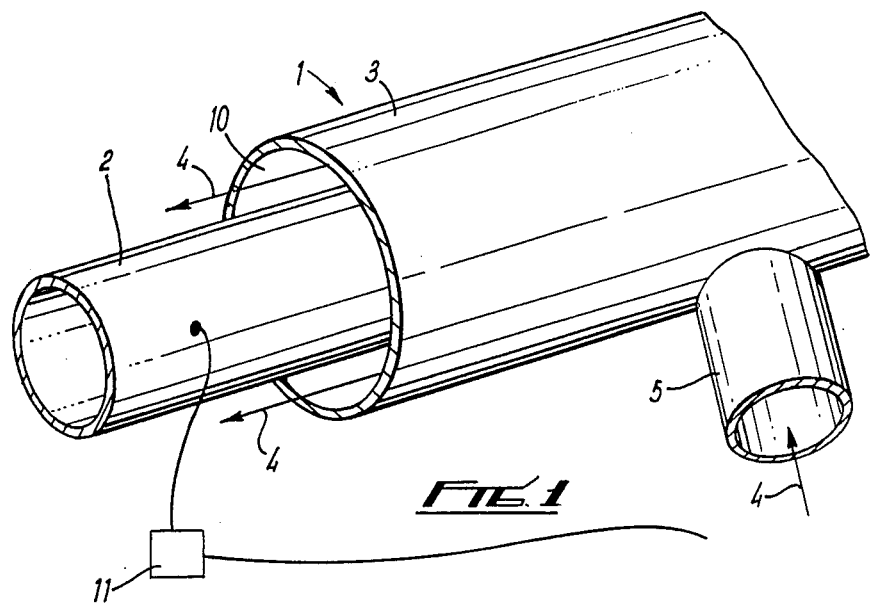
FIG. 1 is a sectional perspective view of a first embodiment of a system in accordance with the present invention.
Figure 2:
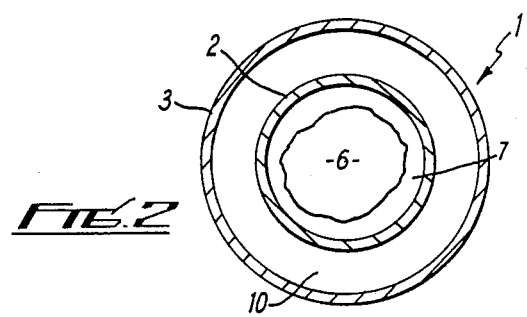
FIG. 2 is a sectional end view of the transfer system of FIG. 1 illustrating the Leidenfrost effect.

Heated air, represented by stream lines 4, is pumped through an inlet pipe 5 into the space 10 between the two tubes 2 and 3. The air 4 warms the inner tube 2 such that when, in this example, liquid nitrogen 6 is passed through the tube 2 the liquid 6 in contact with the tube 2 is vaporised to form a gaseous barrier 7 between the liquid and the wall of the tube 2. This barrier 7 thermally insulates the liquid 6 and thus the nitrogen 6 is maintained in a substantially liquid state, this condition being known as the Leidenfrost effect. Temperature measurement sensors 11 are provided in contact with the tube 2 and are connected electrically with the heating source for the air 4 such that the tube 2 may be maintained at an optimum temperature dictated by, the flow rate and temperature of the heating air 4.

In this way the transfer system 1 can be used to transfer liquid nitrogen from a large insulated reservoir (not shown) to a remote worksite (not shown). As the tubes 2 and 3 remain at approximately room temperature they remain flexible and do not attract condensation from the atmosphere.

Figure 3:
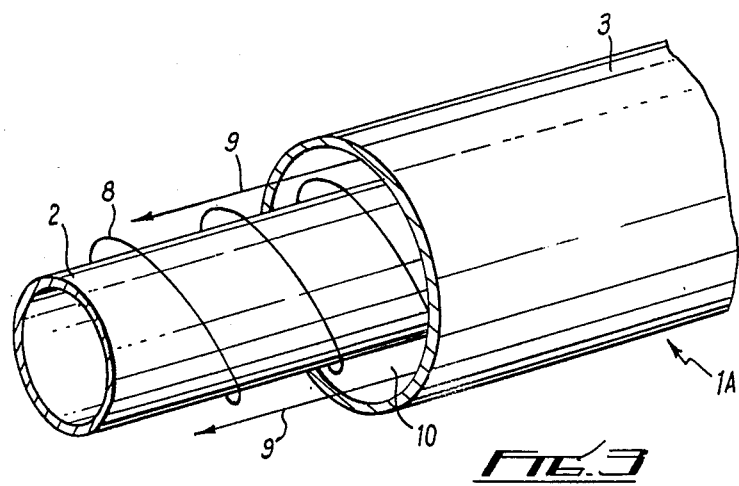
FIG. 3 is a sectional perspective view of a second embodiment of a transfer system in accordance with the present invention.

Referring now to FIG. 3 a second embodiment of a transfer system 1A for use in the transfer of cryogen from a liquid cryogen reservoir to a point of use is similar in construction to the embodiment described above but is provided with an electrical heating element 8 which is used to heat the supplied air 9 passing between the tubes 2 and 3.

In other embodiments of the invention the heating gas is vapourised exhaust cryogen returning from the point of use which is heated by an element similar to that described above and as shown in FIG. 3.

Referring now to FIG. 4, the transfer system 1 of FIG. 1 is used to provide flow of liquid nitrogen at a temperature of $-190°$ C. to a cryoprobe 12, which comprises a nozzle 13 through which the liquid nitrogen emerges from the conduit 2 and a fitting 14 which terminates in a chamber 15. The nozzle 13 and fitting 14 are both made of stainless steel. The chamber 15 contains a loose plug 16 of cotton wool in order to increase the internal surface area of the chamber 15, but not to such an extent that flow of liquid nitrogen into and throughout the chamber is substantially impeded. In use, the cryoprobe 12 is inserted into a body cavity until it is adjacent an area 17 to be treated. The flow of liquid nitrogen is commenced through the tube 2 and proceeds in Leidenfrost flow until it emerges from the nozzle 13 into the chamber 15, where it encounters the cotton wool 16. The very large surface area of the cotton wool ensures effective contact with the liquid nitrogen and thus rapid heat exchange. The liquid nitrogen boils on the cotton wool 16 and on the walls of the chamber 15, thus absorbing latent heat from outside the chamber, and this process continues as long as liquid nitrogen enters the chamber 15 from the nozzle 13. This latent heat absorption has a rapid cooling effect on the environment immediately surrounding the chamber 15, so the chamber wall quickly attains and maintains a temperature of around $-180°$ C. Thus when the chamber wall is brought into contact with the area 17 to be treated, the area is immediately frozen.

FIG. 5 illustrates the cooling rate of the cryoprobe 12 and its subsquent defrosting rate, and it will be seen that an operating temperature of $-180°$ C. is achieved from a starting temperature of 20 C. in around 30 seconds, which is very rapid. Also, the extremely low operating temperature is maintained with stability, which reduces the used for continued monitoring of the cryogen delivery temperature and chamber temperature by an operator.

Modifications and improvements may be made without departing from the scope of the invention.

We claim:

1. A transfer system for use in transferring cryogen from a source to a point of use, comprising a flexible conduit for through flow of cryogenic fluid, heating means external of the flexible conduit arranged to provide heat to a wall of the conduit, and control means associated with said heating means for maintaining the temperature of said wall of the conduit at a level whereby cryogenic fluid flowing through the conduit is maintained in Leidenfrost flow and wherein an operating head comprising a chamber for cryogenic fluid communicates with said conduit, the chamber having an external wall across which heat exchange can take place and filamentary material within the chamber in contact with the external wall of the chamber which provides an increased internal surface area in the chamber on which the cryogenic fluid evaporates to effect heat exchange.

2. A transfer system as claimed in claim 1 wherein the filamentary material within the chamber in cotton wool.

3. A transfer system as claimed in claim 1, wherein the operating head is a stainless steel fitting which is connected to an end portion of the conduit.

* * * * *